US010226298B2

(12) United States Patent
Ourselin et al.

(10) Patent No.: US 10,226,298 B2
(45) Date of Patent: Mar. 12, 2019

(54) SYSTEM AND METHOD FOR COMPUTER-ASSISTED PLANNING OF A TRAJECTORY FOR A SURGICAL INSERTION INTO A SKULL

(71) Applicant: UCL Business PLC, London (GB)

(72) Inventors: Sebastien Ourselin, London (GB); Gergely Zombori, London (GB); Mark Nowell, London (GB); Rachel Sparks, London (GB); John Duncan, London (GB); Roman Rodionov, London (GB); Andrew McEvoy, London (GB); Anna Miserocchi, London (GB); Beate Diehl, London (GB); Tim Wehner, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 15/308,165

(22) PCT Filed: May 14, 2015

(86) PCT No.: PCT/GB2015/051417
§ 371 (c)(1),
(2) Date: Nov. 1, 2016

(87) PCT Pub. No.: WO2015/173571
PCT Pub. Date: Nov. 19, 2015

(65) Prior Publication Data
US 2017/0065349 A1 Mar. 9, 2017

(30) Foreign Application Priority Data

May 14, 2014 (GB) .................................. 1408582.3

(51) Int. Cl.
*A61B 34/10* (2016.01)
*G06F 17/50* (2006.01)

(52) U.S. Cl.
CPC .............. *A61B 34/10* (2016.02); *G06F 17/50* (2013.01); *A61B 2034/105* (2016.02); *A61B 2034/107* (2016.02)

(58) Field of Classification Search
CPC ................ A61B 34/20; A61B 19/5244; A61B 2034/107; A61B 2034/105
(Continued)

(56) References Cited

U.S. PATENT DOCUMENTS

2009/0259230 A1* 10/2009 Khadem ............ A61B 19/5244
606/130

OTHER PUBLICATIONS

Mario Rincon-Nigro et al., "GPU-Accelerated Interactive Visualization and Planning of Neurosurgical Interventions", IEEE Computer Graphics and Applications, Mar. 31, 2013.
(Continued)

*Primary Examiner* — Changhyun Yi
(74) *Attorney, Agent, or Firm* — Park, Vaughan, Fleming & Dowler LLP

(57) ABSTRACT

A system and method are provided for using a computer system to assist in planning a trajectory (960A, 960B) for a surgical insertion into a skull. The method comprises providing the computer system with a three-dimensional representation of the skull and of critical objects located within the skull, wherein the critical objects comprise anatomical features to be avoided during the surgical insertion. The method further comprises providing the computer system with a target location (770, 970) for the insertion within the skull. The method further comprises generating by the computer system a first set comprising a plurality of entry points, each entry point (760) representing a surface location on the skull, and each entry point (760) being associated (2D) with a trajectory (960A, 960B) from the entry point (760) to the target location (770, 970). The method further comprises discarding by the computer system entry points
(Continued)

from the first set to form a second, reduced set comprising a plurality of entry points, wherein an entry point (760) is discarded from the first set of entry points if the entry point (760) has an entry angle which fails a condition for being substantially perpendicular to the skull surface. For each entry point (760) in the second set, the computer system assess the entry point (760) against a set of one or more criteria, wherein the set of one or more criteria includes a risk factor based on the separation between the critical objects and the trajectory (960A, 960B) which is associated with said entry point (760)). This risk factor may be calculated by integrating f(x) along the trajectory (960A, 960B) associated (2D) with the entry point (760), where x represents distance along the trajectory (960A, 960B) to a sample point, and f(x) is a function based on distance from the sample point at distance x to a critical object which is nearest to said sample point.

24 Claims, 6 Drawing Sheets

(58) Field of Classification Search
USPC ........................................................ 606/130
See application file for complete search history.

(56) References Cited

OTHER PUBLICATIONS

Silvain Beriault et al., "Automatic Trajectory Planning of DBS Neurosurgery from Multi-modal MRI Datasets", Medical Image Computing and Computer-Assisted Intervention—MICCAI 2011, Sep. 18, 2011, pp. 259-266.

Elena De Momi et al., "Automatic Trajectory Planner for StereoElectroEncephaloGraphy Procedures: A Retrospective Study", IEEE Transactions on Biomedical Engineering, Apr. 1, 2013, vol. 60, No. 4, pp. 986-993.

Reuben R. Shamir et al., "A Method for Planning Safe Trajectories in Image-Guided Keyhole Neurosurgery", Medical Image Computing and Computer-Assisted Intervention—MICCAI 2010, Sep. 20, 2010, pp. 457-464.

Rangarajan J.R., "Assessment of Variability in Cerebral Vasculature for Neuro-Anatomical Surgery Planning in Rodent Brain", Medical Imaging 2011, Jul. 11, 2011.

International Search Report and Written Opinion from PCT Patent Application No. PCT/GB2015/051417 dated Sep. 29, 2015.

* cited by examiner

SYSTEM AND METHOD FOR COMPUTER-ASSISTED PLANNING OF A TRAJECTORY FOR A SURGICAL INSERTION INTO A SKULL

FIELD OF THE INVENTION

The present invention relates to a system and method for computer-assisted planning of a trajectory for a surgical insertion into a skull (intra-cranial insertion), such as for the pre-operative planning of electrode placement for stereo-electroencephalography.

BACKGROUND OF THE INVENTION

Approximately 20-30% of patients with focal epilepsy are medically refractory to treatment with anti-epileptic drugs. These patients are potential candidates for curative respective surgery [1, 2]. The primary aim of epilepsy surgery is to remove the epileptogenic zone: "the minimum amount of cortex that must be resected (inactivated or completely disconnected) to produce seizure freedom" [3, 4]. The identification of the epileptogenic zone usually involves the placement of intracranial electrodes to record where seizures start and rapidly propagate. Stereo-electroencephalography (SEEG) is the practice of recording electroencephalographic signals via depth electrodes that are surgically implanted into the brain tissue. A significant challenge in epilepsy surgery now is in the treatment of the more difficult patient groups (extratemporal non-lesional), where SEEG is increasingly utilised. This invasive investigation carries the risks of infection, haemorrhage and neurological deficit [5].

Preoperative planning of SEEG electrode placement is a necessary prerequisite to implantation. Important anatomical and functional landmarks of the brain (such as blood vessels, pial boundaries, nerve tracts, etc.) can be identified with advanced neuro-imaging and image-processing techniques. SEEG electrode trajectories are defined by a target area that has to be reached by the electrode and an entry point where the electrode penetrates the skull. Electrode arrangements are planned to achieve adequate cortical coverage and pass through safe, avascular planes. The large number of electrodes required in SEEG and the cumulative risk associated with this implies that computer-assisted planning (AP) would be very useful in such clinical cases.

Previous work on pre-operative planning of depth electrode placement describes approaches to find the optimal path either automatically [6, 7, 8] or by assisting the decision-making process of the neurosurgeon [9, 10, 11]. Another approach [12] has proposed a system to assist at all stages of the planning from the selection of the target point to the selection of a safe entry point that minimizes the risk of hitting a vital structure. In all of these approaches, the operator selects the target point precisely and the time required to compute the optimized paths is generally long. Recently, a high performance solution has been described to enable quantitative estimation of the risk associated with a particular access path at interactive rates [13]. In this approach, graphics processing units (GPUs) are employed to achieve real-time speed, and a custom form of visualization (risk map) is used to aid the planning process.

Nevertheless, the pre-operative planning of electrode placement for stereo-electroencephalography and other such intra-cranial procedures is still frequently viewed as a relatively difficult and time-consuming process.

SUMMARY OF THE INVENTION

The invention is defined in the appended claims.

A method is provided of using a computer system to assist in planning a trajectory for a surgical insertion into a skull. The method comprises providing the computer system with a three-dimensional representation of the skull and of critical objects located within the skull, wherein said critical objects comprise anatomical features to be avoided during the surgical insertion; providing the computer system with a target location for the insertion within the skull; generating by the computer system a first set comprising a plurality of entry points, each entry point representing a surface location on the skull, and each entry point being associated with a trajectory from the entry point to the target location; discarding by the computer system entry points from the first set to form a second, reduced set comprising a plurality of entry points, wherein an entry point is discarded from the first set of entry points if the entry point has an entry angle which fails a condition for being substantially perpendicular to the skull surface; and for each entry point in the second set, assessing by the computer system said entry point against a set of one or more criteria, wherein the set of one or more criteria includes a risk factor based on the separation between the critical objects and the trajectory which is associated with said entry point.

Checking that the entry angle for an entry point is suitably perpendicular (otherwise it becomes much more difficult to drill the entry point through the skull) is computationally quicker than assessing the risk factor based on the separation between the critical objects and the trajectory which is associated with the entry point. Accordingly, a first set of entry points is initially filtered using the entry angle condition, which generally eliminates a majority of this first set of entry points to form a second set containing fewer entry points. The assessment of the risk factor based on separation then only has to be performed on the reduced number of entry points included in the second set, thereby helping with overall computational efficiency in order to provide a real-time and interactive system.

Another method is also provided of using a computer system to assist in planning a trajectory for a surgical insertion into a skull. The method comprises providing the computer system with a three-dimensional representation of the skull and of critical objects located within the skull, wherein said critical objects comprise anatomical features to be avoided during the surgical insertion; providing the computer system with a target location for the insertion within the skull; selecting an entry point representing a surface location on the skull; determining by the computer system for the entry point an associated trajectory from the entry point to the target location; and calculating by the computer system a risk factor for said entry point by integrating f(x) along the trajectory associated with the entry point, where x represents distance along the trajectory to a sample point, and f(x) is a function based on distance from the sample point at distance x to a critical object which is nearest to said sample point.

Conventionally, the risk associated with a trajectory has been determined based solely on the distance of closest approach between the trajectory and a critical object. However, summing the risk factor along length of the trajectory provides a more sophisticated measure of risk. For example, if a first trajectory has only one relatively close approach to a critical object, such a trajectory would now be found to be better than a second trajectory that has several relatively close approaches to critical objects. This enhanced measure of risk may then support a better machine (computer system) based selection of the optimum entry point.

It will be appreciated that the two methods described above can be integrated together into a method that comprises some, or all, features of both methods—for example, to provide a method that discards entry points from a first set to form a second set, and then calculates a risk factor for the entry points in the second set by integrating f(x) along the trajectory associated with the entry point.

The methods described here can be used to support planning a surgical insertion or incision for a wide range of clinical purposes. For example, the surgical incision may be utilised to implant an electrode for performing stereo-electroencephalography (SEEG). In this context, there may be multiple electrodes to insert, each involving the planning a respective surgical incision. Other clinical purposes for planning a surgical insertion may be to insert a stent, to perform deep brain stimulation or a tumour biopsy, the placement of other probes in the brain: eg to drain cysts or ventricles, to introduce a medical laser device into a particular part by a safe trajectory, and/or to deliver focal therapy. (It will be appreciated that this listing of potential clinical purposes is by way of example only, and is not intended to be exhaustive).

It will be appreciated that the precise nature of the instrument or device being inserted will vary according to the particular clinical context. Likewise, the details of the assessment of the one or more criteria, and/or the calculation of the risk factor using f(x), may vary according to the clinical context. For example, the one or more criteria for SEEG may include a cost function based on the proportion of the trajectory associated with an entry point which passes through grey matter compared with the proportion of the trajectory which passes through white matter. This is because the electrode for SEEG, and more particularly, the multiple contacts typically spaced along such an electrode, should be located in grey matter in order to obtain a desired signal. Having a higher proportion of the trajectory in grey matter increases the likelihood that the contacts will be located, as desired, in grey matter. However, this distinction between grey matter and white matter may be less (or not at all) relevant in other clinical contexts, such as for performing a tumour biopsy. Similarly, other aspects of the planning procedure may vary as appropriate according to the clinical context. For example, while major blood vessels are always expected to represent critical objects, the inclusion of certain other anatomical features as critical objects may depend upon the particular clinical context. In addition, the number of target locations to be provided, and the particular mechanism for providing such target location(s), may likewise vary according to the clinical context. Thus in some implementations or situations, a target location may be provided by identifying by the user an anatomical region within the skull, and the computer system then automatically selects a target location within said anatomical region within the skull. This can be done, for example, by the computer sampling the specified region to provide a set of target locations, and then selecting the target location which has a trajectory having the lowest assessed risk. The specified region may comprise, for example, a tumour, or an anatomical structure or feature of interest within the brain.

In some implementations, the function f(x) denotes a cost function that has a value of zero (minimum cost) when the distance from the sample point to the nearest critical object is greater than a first predetermined threshold distance which defines a risk zone, and a value of one (maximum cost) when the distance from the sample point to the nearest critical object is less than a second predetermined threshold distance which defines a safety margin. If the distance from the sample point to the nearest critical object goes below the second predetermined threshold distance, then the trajectory is rejected for encroaching on the safety margin. Conversely, if the distance from the sample point to the nearest critical object goes above the first predetermined threshold distance, then the nearest critical object lies outside the risk zone, and so this sample point in effect does not contribute (or makes zero contribution) to the cumulative risk factor as determined along the trajectory.

In some implementations, the function f(x) rises linearly with distance from the sample point to the nearest critical object between the first predetermined threshold distance and the second predetermined threshold distance. However, other implementations may use a different function for f(x), for example some curved variation of risk with distance from the sample point to the nearest critical object. In addition, f(x) (including any predetermined threshold distances) may vary according to the type or identity of a critical object. For example, a major blood vessel may be defined to have a larger risk zone than a more minor blood vessel, or than some other anatomical feature which is less susceptible to damage.

In some implementations, multiple sample points are defined along the trajectory associated with an entry point, and integrating f(x) along the trajectory comprises summing the value of f(x) at each of the multiple sample points. The number and/or locations of the sample points along the trajectory may be configured as appropriate to give a desired positional resolution. For example, the number of sample points may be in the range 50 to 1000.

In some implementations, the computer system provides a graphical visualization of a trajectory. The visualization illustrates how the distance from a sample point at distance x along the trajectory to the critical object which is nearest to the sample point varies with x along the trajectory. The graphical visualisation may include an indication of the first predetermined threshold distance and/or the second predetermined threshold distance (if defined). This graphical visualization therefore helps a user to understand better any risks associated with the trajectory, in particular, the portion(s) of the trajectory that is/are closest to critical structures.

In some implementations, the graphical visualisation of a trajectory is linked to at least one two-dimensional or three-dimensional view derived by the computer system from the three-dimensional representation of the skull and of critical objects located within the skull. Selecting a sample point location along the trajectory causes the computer system to generate said at least one two-dimensional or three-dimensional view so as to include or be taken from said sample point location. Again this visualization therefore helps a user to understand better any risks associated with the trajectory, especially in terms of their anatomical context.

In some implementations, the condition for being substantially perpendicular to the skull surface requires the entry angle to be within a predetermined angular distance (offset) from the normal to the skull surface at the entry point. This angular distance may represent a maximum offset from the perpendicular of no more than say 10 or 20 degrees. It will be appreciated that the condition for ensuring the practical feasibility of the entry angle may also be based on one or more other (or additional) criteria.

In some implementations, an entry point is also discarded from the first set if the trajectory associated with the entry point exceeds a predetermined length. This predetermined length may depend upon surgical considerations and/or the physical parameters of any device or instrument being used for the incision. In some implementations, an entry point is discarded from the first set if the trajectory associated with the entry point passes through a critical object. This direct hit between a trajectory and an entry point is again relatively inexpensive to identify from a computational perspective. It will be appreciated that the greater the filtering from the first set to the second set, e.g. by using these additional criteria such as maximum length and/or a direct hit, the lower the computational requirements for calculating the risk factor for the remaining entry points in the second set based on f(x) (and/or any other appropriate criteria).

While some implementations utilise entry point angle and/or maximum trajectory length to discard entry points, each such parameter may additionally (or alternatively) be used as a risk factor in assessing the cumulative risk along the trajectory. For example, if an entry point results in a trajectory length which is close to, but below, the maximum permitted length for a trajectory, this may still contribute to the risk or cost associated with the trajectory. Likewise, if an entry point angle is close to, but within, the maximum permitted offset from the normal, this may still contribute to the risk or cost associated with the trajectory.

As mentioned above, in some implementations the computer system may automatically select an entry point and associated trajectory for use in the surgical intra-cranial incision based on said assessment against one or more criteria (risk factors or cost functions, etc). The computer selection may be based on choosing some optimum trajectory, typically the entry point assessed as having the lowest overall risk. The computer system may also provide a graphical representation of the selected trajectory in at least one two-dimensional or three-dimensional view derived by the computer system from the three-dimensional representation of the skull.

As mentioned above, in some circumstances there may be a plurality of target locations. Accordingly, the set of one or more criteria for assessing a trajectory to a given target location may include determining that the trajectory does not conflict with a trajectory to any other target location. Typically, two trajectories are considered to conflict with one another if they pass within a predetermined distance of each other (which may be configurable for different surgical contexts and instruments, etc).

In some implementations, the multiple trajectories for respective target locations are selected after the risk factors have been calculated for each trajectory in the second set, for each target location. The algorithm adds the lowest risk trajectory for each target location in turn, but then checks for conflict after each new trajectory is added. If such a conflict is found, then the next lowest combination of trajectories is evaluated for any conflict (for those targets currently under consideration), and this is repeated until no conflict is found. The algorithm then adds in the lowest risk trajectory for the next target location, and this processing is repeated until a set of trajectories has been found, one for each target location, with no conflict between the trajectories. Such an approach provides a multiple trajectory planning module which enables the automated, simultaneous optimization of electrode trajectories for N target points taking into account electrode interference.

Also provided is a computer program comprising program instructions in machine-readable format that when executed by one or more processors in a computer system cause the computer system to implement any of the various methods as described above. These program instructions may be stored on a non-transitory computer readable storage medium, such as a hard disk drive, read only memory (ROM) such as flash memory, an optical storage disk, and so on. The program instructions may be loaded into random access memory (RAM) for execution by the one or more processors of a computer system from the computer readable storage medium. This loading may involve first downloading or transferring the program instructions over a computer network, such as a local area network (LAN) or the Internet.

Also provided herein is an apparatus comprising a computer system configured to implement the various methods as described above. The computer system may comprise one or more machines, which may be general purpose machines running program instructions configured to perform such methods. The general purpose machines may be supplemented with graphics processing cards units (GPUs) to provide additional processing capability. The computer system may also comprise at least some special purpose hardware for performing some or all of the processing described above, such as determining the visualisations. The computer system may be incorporated into apparatus specifically customised for performing computer-assisted planning of a trajectory for a surgical incision. Such apparatus may also be used to provide support during the surgical operation itself, such as by providing real-time visualisations of the position of an inserted instrument (potentially in relation to the planned trajectory), and/or by providing visualisations of data acquired during the surgical operation.

The approach described herein provides a computer-assisted real-time solution which can be used to first identify the potential entry points by analysing the entry-angle, and then compute the associated risks for trajectories starting from these locations. The entry angle, the total length of the trajectory and distances to critical structures may be presented in an interactive way which is integrated with standard electrode placement planning tools and advanced visualization. The computer-assisted real-time solution helps to improve the planning of intracranial implantation, providing safer trajectories in less time.

A significant application of this approach is in SEEG, which involves the placement of multiple depth electrodes into the brain to record seizure activity and precisely identify an area to be resected. Two important criteria for electrode implantation are accurate navigation to the target area, and avoidance of critical structures such as blood vessels. A typical SEEG implantation contains 8-12 electrodes, each placed to hit a unique target area. The arrangement of electrodes is planned so that each individual electrode meets specific criteria in terms of risk, as well as ensuring that electrodes are placed so as to prevent interference from the other electrodes. The computer-implemented approach described herein for computer-assisted planning facilitates the identification and selection of a good (hopefully optimum) electrode arrangement.

BRIEF DESCRIPTION OF THE DRAWINGS

Various embodiments of the invention will now be described in detail by way of example only with reference to the following drawings.

DETAILED DESCRIPTION

Figure 1:
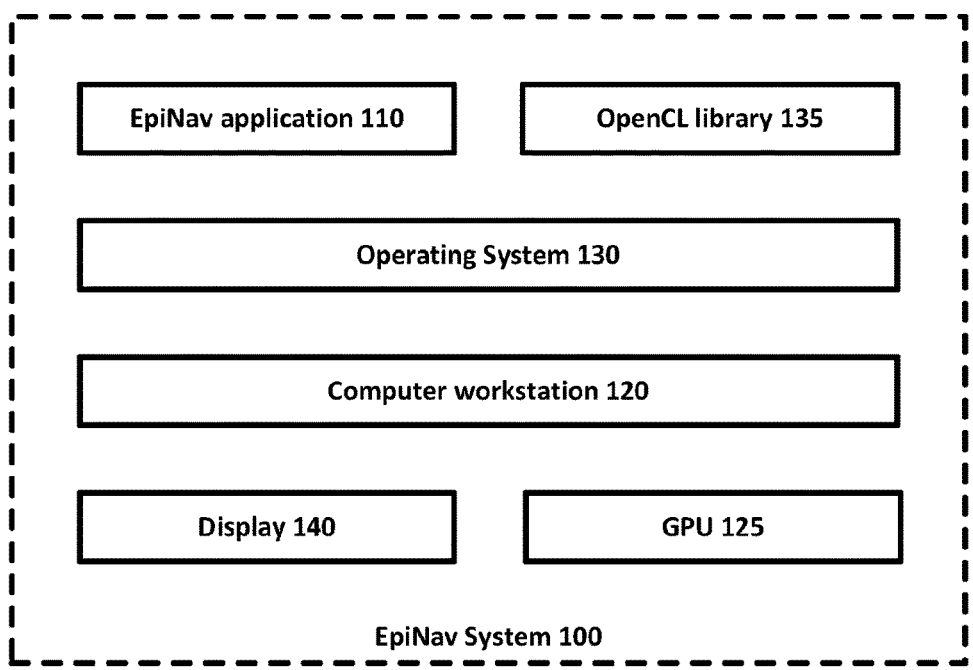
FIG. 1 is a schematic diagram of an interactive tool for computer assisted planning of intra-cranial surgical insertions in accordance with some embodiments of the invention.

FIG. 1 is a schematic block of an interactive and responsive tool (the EpiNav™ system) 100 for the pre-operative planning of SEEG electrode placement in accordance with some embodiments of the invention. The main software application component 110 (the EpiNav application) was developed using a cross platform C++ library NifTK (www.niftk.org) that is based on the Medical Imaging and Interaction Toolkit (MITK, www.mitk.org) [14]. The software runs on a (modern) computer workstation such as a personal computer (PC) 120 which is provided with (at least one) display 140, and a (modern) graphics card (graphics processing unit, GPU) 125 which functions as general-purpose parallel processor. (The PC 120 will generally also be provided with standard accessories, such as a mouse, keyboard, etc, not explicitly shown in FIG. 1). The PC has an operating system 130, such as Mac OS X, Linux or Windows, and also has the OpenCL (Open computing language) library 135 from the Khronos Group installed to enable the execution of applications that utilise parallel programming (the GPU should be compatible with the installed version of OpenCL, such as v1.1). In operation therefore, the EpiNav application 110 utilises the OpenCL library 135 to perform processing on the GPU 125. The EpiNav application 110 also utilises the capabilities of the PC itself 120 (which includes one or more processors, not explicitly shown in FIG. 1) for performing additional processing. It will be appreciated that the configuration illustrated in FIG. 1 is provided by way of example only, and the skilled person will be aware of many other possible implementations on single computers (machines), distributed across two more computers, etc.

In order to help provide a faster planning process for SEEG electrode placement that also ensures the safety of the resulting implantation plan, the EpiNav system 100 assists in satisfying the following conditions:

i) critical anatomical structures, such as blood vessels, nerve tracts, and brain functional areas, are clearly identifiable using one or more visualization mechanisms, such as a synched ortho-views (2-D images representing orthogonal planes), 3-D rendering, and/or a Probe Eye view (as seen along an electrode trajectory).

ii) no trajectory intersects any critical tissue in order to avoid harming the patient.

iii) each trajectory is further than a specified safety margin from the critical tissue (and from other trajectories). The safety margin is derived, at least in part, from the accuracy of the surgical procedure for implanting the electrodes.

iv) each trajectory is as short as possible. (We assume for the time being that only the tip of the electrode is meant to hit the target).

v) the entry angle of each trajectory is generally as close to 90 degrees (i.e. normal to the surface) as possible, since this allows a more robust implementation of the planned entry angle during the surgical procedure. For example, the system may constrain the entry angle to within a specific range from the normal.

The EpiNav system 100 provides computer-assisted planning in view of the above considerations to support target and entry point selection, and also adjustment of the target and entry point selection on the basis of real-time interaction by a user. The entry points are constrained to follow the skull surface. The safety criteria and other operational conditions, such as the minimum distance to a critical structure, the minimum distance to any other trajectory, the range of acceptable entry angles, the maximum length of a trajectory, and/or the variation of risk with distance to a critical structure (assuming that the minimum distance is satisfied), can be configured by a user if so desired.

Critical Structures

Identifying critical objects is very important for the successful estimation of a safe trajectory. These critical objects are determined from clinical images obtained using one or more imaging modalities that have been acquired along the presurgical diagnostic pathway. The EpiNav system 100 imports all objects representing clinically relevant landmarks into an interactive visualization workstation, i.e. system 100, adopting a generally similar approach to that described in [15]. The potential (clinically relevant) landmarks include white matter tracts (e.g. cortico-spinal tract, optic radiation tract) derived from diffusion tensor imaging (DTI, also known as diffusion MRI) data, lesions, eloquent cortex (e.g. language or motor areas) derived from functional magnetic resonance imaging (fMRI), areas of ictal hyperperfusion derived from single photon emission computed tomography (SPECT), and areas of hypometabolism derived from positron emission tomography (PET) images, and ictal or interictal electroencephalography (EEG) and/or magnetoencephalography (MEG) sources. Likewise, information about blood vessels (vasculature) may be extracted from images, as described in more detail below.

An image of the skull, which in particular provides information about the surface of the skull, is also provided to determine the accurate location of each entry point on the skull surface and to compute the entry angle of the trajectory. Such a representation of the skull surface may be derived, for example, from computed tomography data (CT) and/or from computed tomography angiography (CTA) data, or from pseudo CT data synthetized from an MRI scan [16]. The skilled person will be aware of various other mechanisms for acquiring or synthesising a suitable image of the skull. The skull image is then used to determine the surface of the skull, which represents in effect the set of entry points for SEEG electrode placement.

Note that the initial identification of the critical structures may be performed outside the EpiNav system 100, thereby allowing the identification to be performed on platforms that are particularly suited to analysing the different respective types (modalities) of imaging data. However, in some implementations, at least some of this identification may be performed within the EpiNav system 100 itself. For example, the EpiNav system 100 incorporates the following modules to support the identification of critical structures: NiftySeg component: this provides a fully automatic brain parcellation from clinical T1 images, and is able to extract the cortical surface, identify sulcii and pial boundaries, CSF (ventricles) and to separate gray matter from white matter. VesselExtractor component: this allows the automatic segmentation of veins and arteries from 3D Phase Contrast MR, Post-contrast time-of-flight (TOF) MR and CTA images. This component detects vessel-like structures without any user interaction, and automatically classifies the blood vessels based on the diameter and discards of extra-cranial vessels. The vessel-extractor component can also suppress small and unconnected fragments and it is able to reconstruct the vessel network, separating veins and arteries.

After the critical structures (objects) have been loaded into (and/or determined by) the EpiNav system 100, each such structure is converted into a 3D surface mesh object representation (or into any other appropriate representation of the shape of the critical object). In other implementations, the conversion into 3D surface mesh object representation for at least some critical objects may be performed outside the EpiNav system 100, with the mesh representations themselves then being loaded (imported) into the EpiNav system 100. The use of a mesh object representation helps to provide more efficient distance calculation from a trajectory to the surface of a critical object; in particular, the distance can now be calculated based on the distance from the trajectory to the mesh representing the surface of the critical object (rather than working directly with the raw image data for such calculations). Furthermore, the ability to import a mesh representation into the EpiNav system 100 allows the same mesh representation to be used consistently in different clinical tools.

Figure 2:
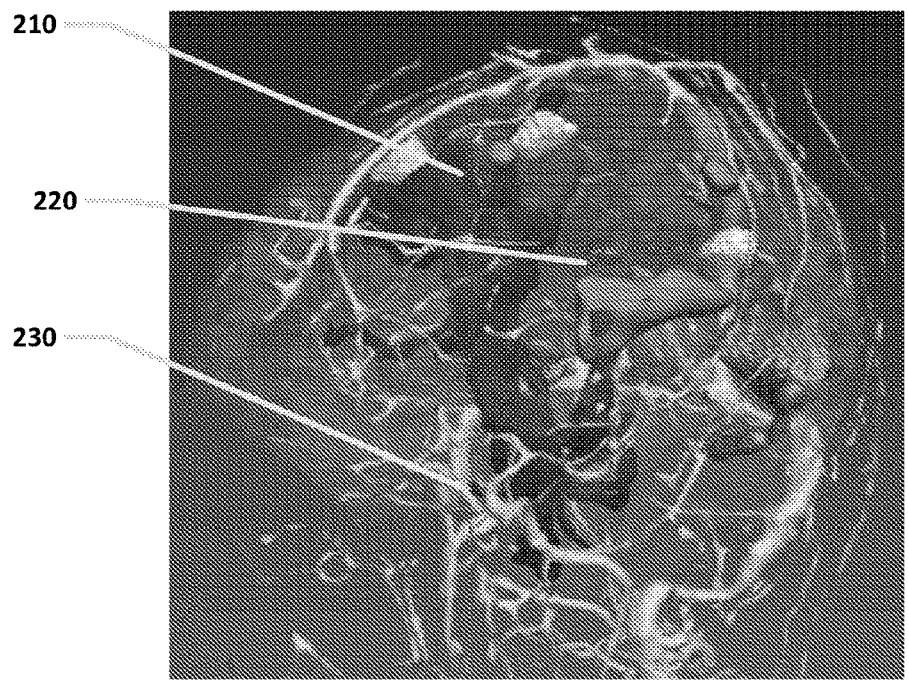
FIG. 2 is an example of a visualisation provided by the tool of FIG. 1 comprising a 3-D representation of the brain and associated structures.

The critical structures can then be displayed (visualised) on the display 140. The critical structures may be coloured using a colour scheme to emphasise the different types of objects. An example of such a visualisation is shown in FIG. 2, in which blue is used to denote the cerebrospinal tract 210, orange is used to denote the lip motor 220 (from fMRI), and cyan is used to denote veins (230). (It will be appreciated that the underlying data in FIG. 2 corresponds to a three-dimensional (3D) image or set of structures, while FIG. 2 itself shows a 2-dimensional (2-D) visualisation of this three-dimensional image data).

Trajectory Planning

The planning process starts with the selection of the target point for locating an electrode, using a reference image based on the three-dimensional image data (such as illustrated in the visualisation of FIG. 2). If the EpiNav system 100 is provided with a detailed brain parcellation map, which breaks the brain down into various anatomical regions, this parcellation can also be provided for the reference image, for example, by different highlighting and/or colouring of the various anatomical regions of the brain. The reference image also incorporates the position of the skull surface, as derived from the skull image.

The EpiNav system 100 provides 2D and 3D views of the reference image on display 140, including parcellation if available. The skull surface may be omitted from the displayed reference image if so desired to provide better visualisation of the critical objects internal to the skull. A user can then select or place a target point by clicking, e.g. with a mouse, on a desired location within the space of the reference image using one of these 2D or 3D views. The target point can be placed to any location within the space of the reference image.

Each trajectory may be individually named and coloured and its length is calculated automatically. Multiple trajectories can be placed within a session. The individual trajectories may be grouped into "plans", where a given plan can contain any number of trajectories. The visibility of the trajectories (show/hide) on the various visualizations can be controlled on an individual basis and/or on a per plan basis. If all of a plan is hidden, then all of its trajectories become hidden too.

Entry Points Search and Risk Analysis

After the target point has been selected, the entry points can be selected manually by the user and/or automatically by the EpiNav system 100. An entry point can only be placed onto the skull surface (a 3D representation of the skull surface is derived from the input images, as described above). However, the EpiNav system 100 allows a user to place an entry point by clicking on an arbitrary location of the 2D or 3D display. The target and entry points are then connected, and the line of the trajectory is automatically extended from the entry point until the line intersects with the skull surface outline. This intersection point defines the entry point on the skull surface, and also the trajectory from the entry point to the target point. The trajectory can be analysed to identify the risks associated with this trajectory. The user can configure the required minimum distance between two trajectories and also the minimum distance from a trajectory to any critical structure (if these requirements aren't met the user, will be warned to re-consider the placement of the entry point and/or the target point).

The EpiNav system 100 is also able to analyse automatically the topology of the critical structures and to offer a set of potential entry points that represent minimal risk. This entry point search is a fully automated method that is implemented on the GPU 125. The method takes the mesh representation of the skull surface as the input and processes each vertex of the index, so that the sampling space and rate when searching for possible entry points are defined by the number and location of vertices in the skull model. The risk associated with each potential trajectory (from a potential entry point to the target point) is evaluated in real-time using the GPU 125, and unsuitable (e.g. high risk) candidates are ruled out.

An entry point search is performed to find the set of potential entry points that represent minimal risk. The first portion of this search involves a proximity search to find all points on the skull surface which are within a predetermined distance of the target point, where the predetermined distance reflects a maximum length for a trajectory. This maximum length may in turn be specified based on the physical characteristics and/or operational requirements of the electrodes that are being inserted.

The entry point candidates from the proximity search are then analysed to find the angle of entry by computing the deviation between the direction vector of the trajectory and the surface normal of the skull at the point of entry. From a practical (surgical) point of view the entry angle should be as close to perpendicular as possible, otherwise it becomes increasingly difficult to drill the keyhole through the skull. Therefore, if the entry angle of an entry point is outside a user-configured range (e.g. more than 10 or perhaps 20 degrees from perpendicular), the entry point is ruled out.

Since the analysis of trajectory length and entry angle is computationally inexpensive, it is feasible to perform such analysis for all possible entry points (i.e. for all nodes or vertices of the surface mesh) and then to disqualify (filter out) those entry points for which the trajectory is too long (greater than some threshold) or the entry point angle is too great (further from the perpendicular than some threshold angle, such as 10 degrees). Each of the remaining entry point candidates, i.e. which are suitably close to the target point and have an acceptable entry angle, is then checked for any collision with the critical structures. If the position of an entry point does not allow straight access to the target point without collision with any critical structure, it is disqualified from the further analysis. This evaluation procedure further reduces the number of candidate entry points.

The above filtering of entry point candidates significantly reduces the number of remaining entry point candidates (compared with the original number of entry point candidates), thereby permitting a more detailed, automated, risk analysis of the remaining entry point candidates while still maintaining real-time and interactive performance. Note that previously published risk metrics have assigned risk based on the shortest Euclidean distance to a critical object from any point on the trajectory. In contrast, the metric used for the present approach is based on a cumulative risk profile which may be obtained along the full length of the trajectory.

The automated risk analysis starts by investigating the distance from each trajectory to the critical structures. For each potential trajectory from a candidate entry point to the target point (target location), a predetermined number of sample locations are considered along the length of the trajectory. (In the current implementation, the predetermined number of sample locations is 256, but other implementations may use a smaller or larger number, and/or may make this number configurable by the user).

The EpiNav system 100 now calculates, for each sample point, the minimum distance to the critical structures (one at a time). The minimum distance to the nearest critical object for that sample point, which is referred to as the critical distance, is then recorded in an array which lists, for each sample point along the trajectory, the corresponding critical distance.

Once the critical distances have been identified for each potential trajectory, an overall risk computation is performed using a new integrative risk metric that quantifies the level of risk on a 0-1 scale (0—no risk; 1—the highest risk which must be avoided). This metric can be extended, if so desired, to include one or more additional factors as discussed above, such as distance and angle of entry, as well as whether the electrode contacts are in grey matter.

A trajectory is considered too risky if the minimum distance to any critical structure, for any sample point on that trajectory, is less than a preset distance: $d_{min}$, which can be considered as defining a safety margin. Conversely, if all sample points on a trajectory lie further from a critical structure than a distance $d_{max}$, which can be considered as defining the boundaries of a risk zone, then the critical structure represents no potential harm to the trajectory. Note that the values of $d_{min}$ and $d_{max}$ can be configured by the user as required in the EpiNav™ system.

We can therefore quantify the overall level of risk arising from proximity to critical structures or objects according to the following:

$$R_{dist} = 1/L \int_{entry}^{target} f(d(x) - d_{min}) dx \quad (Eq\ 1)$$

where x represents the distance along the trajectory to a given sample point, L represents the total distance from entry to target (i.e. the integral of dx from entry to target) d(x) represents the critical distance for the sample point at distance x, and $f(y)$ is a function which decreases monotonically from $f(y)=1$ at $y=0$ to $f(y)=0$ at $y \geq d_{max} - d_{min}$. Note that:

a) $f(y)$ may be specified to have a simple straight line shape, or may have some other form if this better represents the variation in risk with critical distance;

b) for y<0, $f(y)$ can be considered as undefined, or infinite. This value for y (which represents $d(x) < d_{min}$), would imply that the critical distance at this sample point is less than the safety margin, $d_{min}$, and hence this trajectory should be eliminated;

c) Equation 1 yields a value for $R_{dist}$ which is in the range of 0-1; and d) Equation 1 is presented as an integral, which in effect assumes a continuous (infinite) distribution of sample points along the trajectory, but it can be readily converted into a summation for a finite number of sample points.

Figure 3:
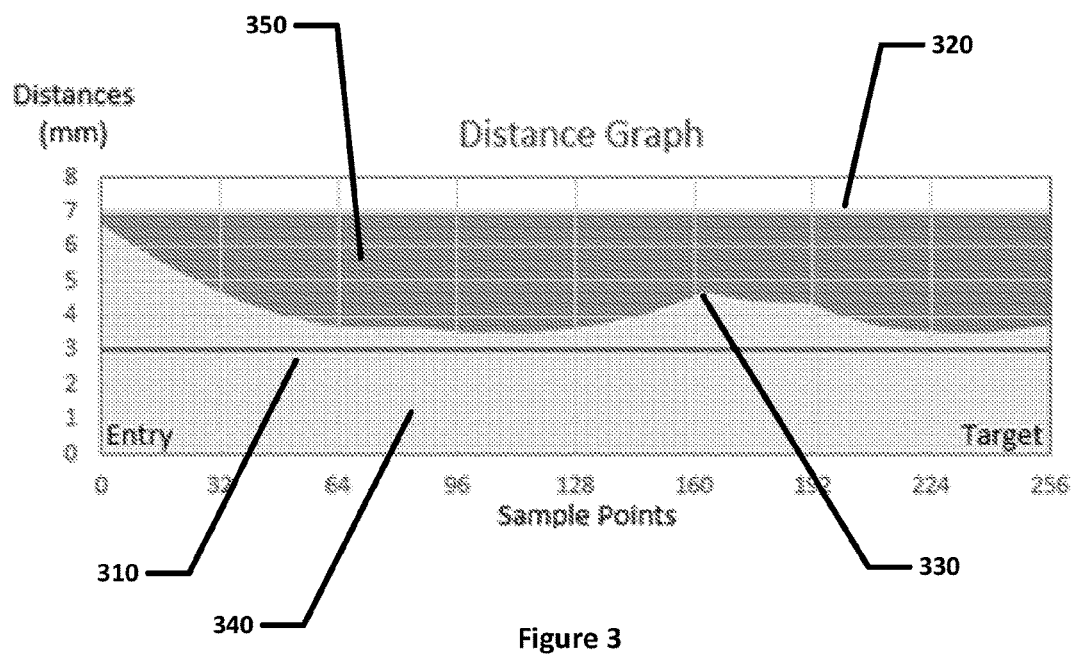
FIG. 3 is an example of a visualisation provided by the tool of FIG. 1 comprising a distance graph showing the variation in risk, in terms of distance to a critical object, along a trajectory for a surgical insertion.

The application of Equation 1 is illustrated in FIG. 3, which is a graph having the sample point number (in effect, the distance x) as abscissa and the critical distance (in millimeters) as the ordinate. In FIG. 3, the red line 310 represents the required safety margin, $d_{min}$ (3 mm in the particular example of FIG. 3), while the green line 320 represents the size of the risk zone, $d_{max}$ (7 mm in the particular example of FIG. 3). The value of the critical distance d(x) at each sample point is denoted by the line 330 representing the boundary between the lower, light grey region 340, and the upper, blue region 350. Note that the critical distance line 330 is always above the minimum safety margin, $d_{min}$, which is necessary to avoid elimination of the route. If we assume that $f(y)$ has a simple linear form, so that risk contributed in respect of a given sample point is proportional to the distance of critical distance line 330 beneath the risk zone line 320 for that sample point, then the quantity $R_{dist}$, as specified in Equation 1, represents the ratio of (i) area 350 shade blue in FIG. 3, i.e. between the risk zone line 320 and critical distance line 330, to (ii) the total (rectangular) area between the risk zone line 320 and the safety margin line 310.

The (predicted) risk associated with (emanating from) the entry angle can be similarly expressed as a risk, $R_{angle}$, based on the range of accepted values, likewise the risk associated with (emanating from) the length of the trajectory: $R_{length}$. For example, an offset angle from the perpendicular of 0 degrees may be assigned a risk of 0, while an offset of (e.g.) 10 degrees may be assigned a risk of 1 (entry points with a higher offset angle would have already been eliminated); intermediate offset angles are then assigned an appropriate intermediate risk value. An analogous approach can be used to assign a risk to the trajectory length.

These independent risk components can be combined by applying appropriate weighting factors ($w_i$) to give a total or overall risk:

$$R_{total} = w_1 R_{dist} + w_2 R_{angle} + w_3 R_{length} \quad (Eq\ 2)$$

-continued where $\sum w_i = 1$ and $R_i \in [0 \sim 1]$

This final metric $R_{total}$, which has a value between 0 (lowest risk) and 1 (highest risk) describes the overall quality of (risk associated with) a given trajectory. (The risk can also be regarded as a form of cost function, where a low risk or cost is desirable).

For the EpiNav system 100, the risk evaluation is performed on the GPU 125. In particular, the entry-angle computation and ray-triangle intersection methods (used for determining the distance between a sample point and a mesh surface) are achieved using an efficient parallel implementation based on the OpenCL kernels 135. To assist the proximity search and distance evaluations in completing in real-time, a Bounding Volume Hierarchy (BVH) is built over the triangle vertices or cells of critical structures. A BVH is an acceleration data structure that allows the fast traversal of large datasets containing 3D points. The adoption of BVH for proximity analysis using GPU hardware is described in [13, 17, 18] (the traversal itself is also implemented using OpenCL 135).

In some implementations, the EpiNav system 100 further includes a risk analysis module which is used to perform real time analysis of critical distances, entry angle (as above) and grey matter/white matter ratio. This latter parameter is significant, since it is generally desired to place the electrodes used for SSEG in grey matter (for clinical reasons to best detect the desired signals). In addition, a typical electrode may in practice have multiple contacts which are spaced along the length of the trajectory. Having a high grey matter/white matter ratio improves the likelihood that these electrode contacts are situated in grey matter (as desired) rather than in white matter. If this ratio is below a configurable threshold, the user may be warned to re-consider the placement.

It will be appreciated that there are other ways of determining a risk or cost associated with grey matter/white matter. For example, if the particular number and location of the contacts on a given electrode are known (e.g. based on manufacturer specifications), then it can be determined how many (or what fraction) of the contacts are located in grey matter for a given trajectory, and then set the cost or risk accordingly.

As described above, the risk analysis is performed automatically to determine a final metric $R_{total}$ that describes the overall quality of any given trajectory. More particularly, this metric can be determined for a large number of potential trajectories. Safe zones and no-go areas can be derived as appropriate.

Figure 4:
FIG. 4 is an example of a visualisation provided by the tool of FIG. 1 comprising a 2-D Probe View as seen from a location along a trajectory for a surgical insertion.

After the associated risks have been computed and the quality of all the potential trajectories has been assessed, the risk values may be visualized. As described below, the EpiNav system 100 is provided with a display 140 which is used to present a visualization of risk. For example, the EpiNav system 100 supports a colour coded display of the associated critical distance to each sample point along the trajectory, see, for example, FIG. 5 below, and this display may be synched with other forms of visualization, such as a Probe Eye view as shown in FIG. 4.

Multiple Trajectory Planning

In a practical application of SEEG, it is generally desired to implant multiple electrodes. These electrodes should not interfere with one another. Accordingly, the placement of each entry point should also take into consideration the placement of the other entry points (for other target locations). One way of achieving this is to determine an entry point using the above approach for each target point in turn. Trajectories that have already been determined for previous target points can then be treated as critical structures to be avoided (as for the other critical structures), as each new trajectory is determined. Although this approach is feasible, it is dependent on the ordering in which the target points are chosen for determining a trajectory, and may therefore not provide the best overall solution.

The EpiNav system 100 therefore incorporates a multiple trajectory planning process which avoids such sensitivity on target point ordering. The process starts with the user selecting the desired set of N target points $T_i : i \in \{1, \ldots, N\}$. For each target point in this set, the entry point search and risk analysis procedure is run independently to obtain a set of M potential entry points $E_{i,j} : j \in \{1, \ldots, M\}$—i.e. entry points that are not excluded or filtered out by virtue of being too long, having an unacceptable entry angle, or going directly through a critical structure to get to the target point. Each potential target/entry point pair in a set M is represented by a trajectory $\overline{T_i E_{i,j}}$. The risk analysis procedure described above then returns a risk score $R_{i,j}$ that describes the overall quality for each $\overline{T_i E_{i,j}}$ trajectory in M (note $R_{i,j}$ corresponds to $R_{total}$ in Equation (2) above).

The multiple trajectory planning procedure seeks to find an optimal combination of trajectories for all of the N target points such that they do not interfere with one other. Trajectory interference is considered to occur if the minimum distance between any two trajectories is smaller than a "Trajectory Margin" distance: $d_{min}$. This trajectory margin distance can be configured by the user, and may be set as appropriate to be the same as, or different from, the $d_{min}$ used to specify the safety margin around the critical structures.

The optimal combination of N trajectories can then be calculated as a combination of the risk scores for each trajectory:

$$R_{all} = \min_{R_{all}} \frac{1}{N} \sum_{i=1}^{N} R_{i,j} : j \in \{1, \ldots, M\} \qquad \text{Equation (3)}$$

subject to $D(\overline{T_i E_{i,j}}, \overline{T_k E_{k,j}}) > d_{min} : \forall i \in \{1, \ldots, N\}, \forall k \in \{1, \ldots, N\}, i \neq k$. Note that $D(\overline{T_i E_{i,j}}, \overline{T_k E_{k,j}})$ represents the minimum distance between the two trajectories $\overline{T_i E_{i,j}}$ and $\overline{T_k E_{k,j}}$. The final metric $R_{all}$ describes the overall quality (risk or cost) of the trajectory combination on a 0-1 scale (0—no risk; 1—the highest risk which must be avoided).

To support real-time optimization of $R_{all}$, a dynamic programming depth-first search algorithm is utilized. The algorithm starts with an initial value of n=1, and proceeds as follows:
1) Find the combination of n trajectories having the (next) lowest risk score.
2) Evaluate if $D(\overline{T_i E_{i,j}}, \overline{T_k E_{k,j}}) > d_{min}$ for all n trajectories.
3) If false return to (1); if true find the next lowest risk score for n+1 trajectories (and increment n).
4) Return when a valid configuration for n=N is found.

In this approach, the target points or trajectories are effectively added in one at a time. For n=1, step 1 is simple, it just involves selecting the trajectory for that target location which has the lowest overall risk factor (on an individual basis). For n=1, step 2 necessarily returns true (because a single trajectory cannot have a conflict with itself). We therefore return to step 1, and include the trajectory for a second target point, in particular the trajectory which has the lowest overall risk factor (on an individual basis) for this second target point. However, if a conflict is found at step 2, i.e. the distance between the new trajectory and the existing (already included) trajectory is less than $d_{min}$, then selected entry points are reconsidered at step 1 for both of the target entry points (not just the newly added target point) to find the (next) lowest combination of risk factors for the two target locations. This procedure is then repeated, adding in another target location at a time, until all N trajectories have been determined. Note that by considering only the lowest valid combination of trajectories at step 1 of each iteration, the output of this algorithm produces the optimal (in terms of risk score minimization) configuration of electrodes.

Visualization

After the associated risks have been computed as described above to determine the quality of all the potential entry points and their corresponding trajectories, the EpiNav system 100 allows these risk values to be visualized. In particular, the EpiNav system supports standard orthogonal views (2D planes: axial, coronal, sagittal), together with a 3D visualization view (volume/surface rendering) in a 2×2 layout.

The EpiNav system 100 also supports a "Probe Eye View" display and a "Distance Graph". The Probe Eye View displays an oblique plane (2D) that is always perpendicular to the line of the trajectory. FIG. 4 illustrates an example of this Probe Eye view (based on the same critical structures as shown in FIG. 2). The Distance Graph corresponds to FIG. 5, and is generally similar in format to FIG. 3 as discussed above.

The visibility of an object in the 2D and 3D views can be individually enabled or disabled. Colour and opacity settings are consistent across all the different forms of visualisation. In addition, a cursor location may be synched between the 2D and 3D views, such that clicking on a surface point in the 3D window will update the position of all the 2D views. Conversely, clicking on a 2D location in one of the ortho (gonal) views updates the slice in the other two 2D views, as well as the 3D locations of the ortho-planes in the 3D window. The Probe Eye view is likewise linked to the other forms of visualization. For example, when changing slice in the Probe Eye view, the axial-coronal-sagittal planes (i.e. the 2D ortho-planes) and the 3D display will also re-position to show the currently selected point along the trajectory.

Planned trajectories are visualized in both 2D and 3D. Within the 2D windows the entry point and target point are flagged—for example, the entry point is represented using a cross, while a circle represents the target point. The way in which the trajectory line itself is depicted depends on the position of the current view-plane relative to the start point and the end point. If the current view plane intersects with the trajectory line, then the intersection point is marked e.g. by a small square. This marker divides the trajectory into two sections: one that falls "above" the view-plane (towards the camera position), while the second falls "behind" the view plane. The first section is represented by a solid line and the second section is drawn using a dashed line. On the other hand, if the view plane does not intersect with the trajectory, and the whole length of the trajectory falls "above" the view plane, the whole line is drawn with a solid line but with reduced opacity (say 0.25). Similarly, if the whole length of the trajectory falls "behind" the current view-plane, then the trajectory is drawn with a dashed line but again with reduced opacity.

In the 3D window, the target point is represented by a sphere while the entry point is marked by a 3D arrow shape with the tip aligned onto the entry point. The trajectory line itself is depicted using a cylindrical object (tube). Individual contacts of an electrode may also be visualized (typically a single electrode is provided with multiple contacts). The contacts are numbered starting from the contact which is closest to the tip of the electrode and the numbering is overlaid on the representation of the electrode (for both 2D and 3D). The exact number of the contacts per electrode, plus the precise location of each contact, are determined using an electrode library, which in turn is derived from specifications provided by the electrode manufacturers.

The electrode visualization module is also able to highlight the brain areas that are potentially contributing to the signal of a selected electrode contact in both the 2D and 3D views. This is done by aligning a semi-transparent cylindrical object over the electrode contacts, where the diameter of the cylinder is equal to the sampling radius of the electrode.

Figure 5:
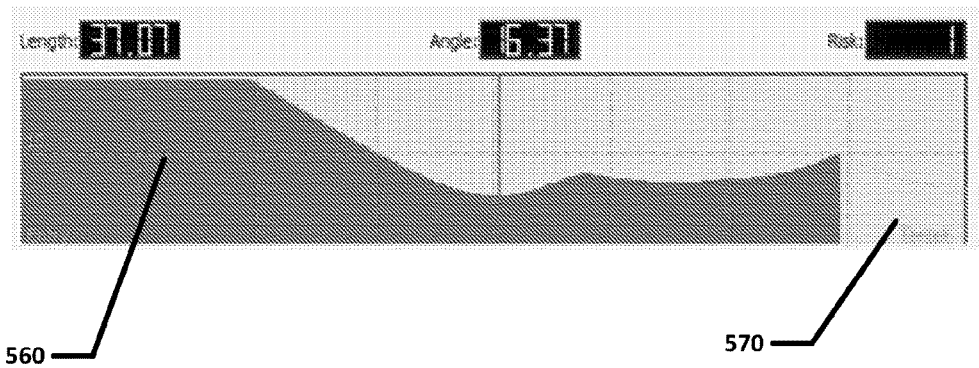
FIG. 5 is another example of a visualisation provided by the tool of FIG. 1 comprising a distance graph similar to that shown FIG. 3.

Returning to FIG. 5, this provides (like FIG. 3) a visual representation of the minimal distance information for a trajectory in form of a graph, in which the length of the graph (horizontal axis) corresponds to the length of the trajectory, while the height of the bars (vertical axis) represents the distance to the nearest critical structure for that particular point along the trajectory. The graph of FIG. 5 may be scaled in a non-linear fashion along the vertical axis to focus the representation on the most important sections i.e. within the Risk Zone. This graph is colour-coded so that the red region 560 shows the portion of the trajectory where the critical distances extend to an artery, while the cyan region 570 shows the portion of the trajectory where the critical distances extend to a vein. As shown in FIG. 5, the EpiNav system 100 also displays, above the graph, the length of the path, angle of entry, and the predicted risk for this trajectory.

The display of FIG. 5 enables a user to adjust or configure various parameters, such as $d_{min}$ (the safety margin) and $d_{max}$ (the risk zone), either by numerical input, and/or by dragging and dropping the respective lines as depicted in FIG. 3. The distance graph of FIG. 5 is updated in real-time in response to such changes, and also in response to other changes, such as moving the entry point to a different location (such as in a linked 3-D view).

The EpiNav system 100 supports linked visualization components (similar to [12]), in which a cursor location is synchronised between all visualization components. For example picking a surface point in a window showing a 3D view also updates the cursor position of all the other (typically 2-D) views. Similarly, clicking on (selecting) a sample point in the Distance Graph of FIG. 5 will update the displayed slice in the Probe Eye View of FIG. 4 so as to display the oblique plane perpendicular to the trajectory at the selected sample point. Similarly, clicking on (selecting) a sample point in the Distance Graph of FIG. 5 will also update the slice positions in the 3 orthogonal plane views listed above. Conversely, changing the slice in the Probe Eye View display will update the cursor position in the Distance Graph (as well as in various other views).

Such visualizations help a user to identify riskier sections of the planned trajectory. For example, by clicking on a riskier section of the Distance Graph of FIG. 5 where the critical distance is relatively low (close to the safety margin), the associated 2D and 3D views will be presented for review. Moreover, the information shown in the distance graph of FIG. 5, including the entry angle, length, risk and slice position are updated in real time if the trajectory is adjusted.

Potential entry points are displayed by the EpiNav system 100 using a colour scheme in which the risk value (as per Equation (2)) is linearly mapped onto a colour lookup table that extends from red to green, where red corresponds to high risk while green corresponds to low-risk. The locations of the potential entry points are then marked on the skull surface by colouring their location according to the risk associated with that entry point.

Figure 6:
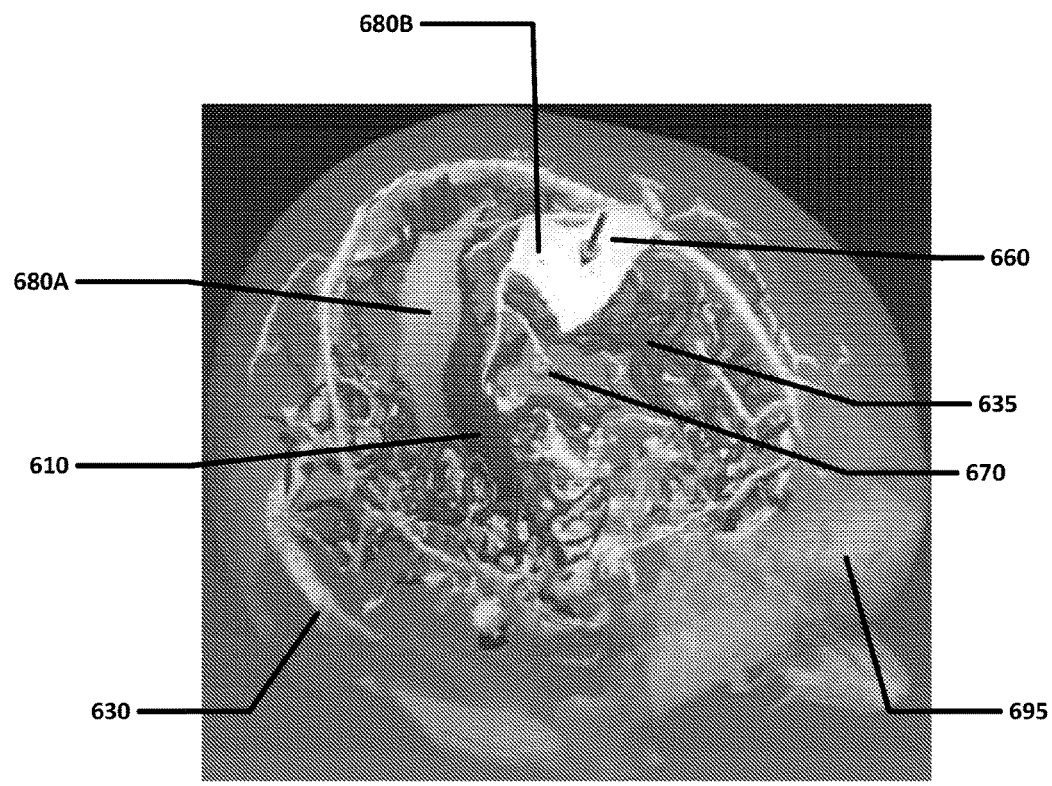
FIG. 6 is an example of a visualisation provided by the tool of FIG. 1 comprising a 3-D representation similar to that shown FIG. 2, but annotated with a target location, entry point regions that have an acceptable risk for that target location, and a particular selected entry point.

FIG. 6 presents an example of this visualization which shows as critical objects the cerebrospinal tract 610 (blue), veins 630 (cyan) and arteries 635 (red). The assessment of risk factor as identified two regions of the skull for which there are potential entry points, depicted by regions 680A and 680B. The region 680A is associated with a higher risk than region 680B, and hence region 680A has a greener colouration than region 680B. The desired target location (which was picked at random) is depicted by the small green sphere 670, and the currently selected entry point, which corresponds to the lowest risk, plus the associated direction of insertion for the trajectory, are indicated by the arrow marker 660. of the potential entry points for a given target point 610 (which was picked at random). The skull itself is shown semi-transparently in the background 695.

Figure 7:
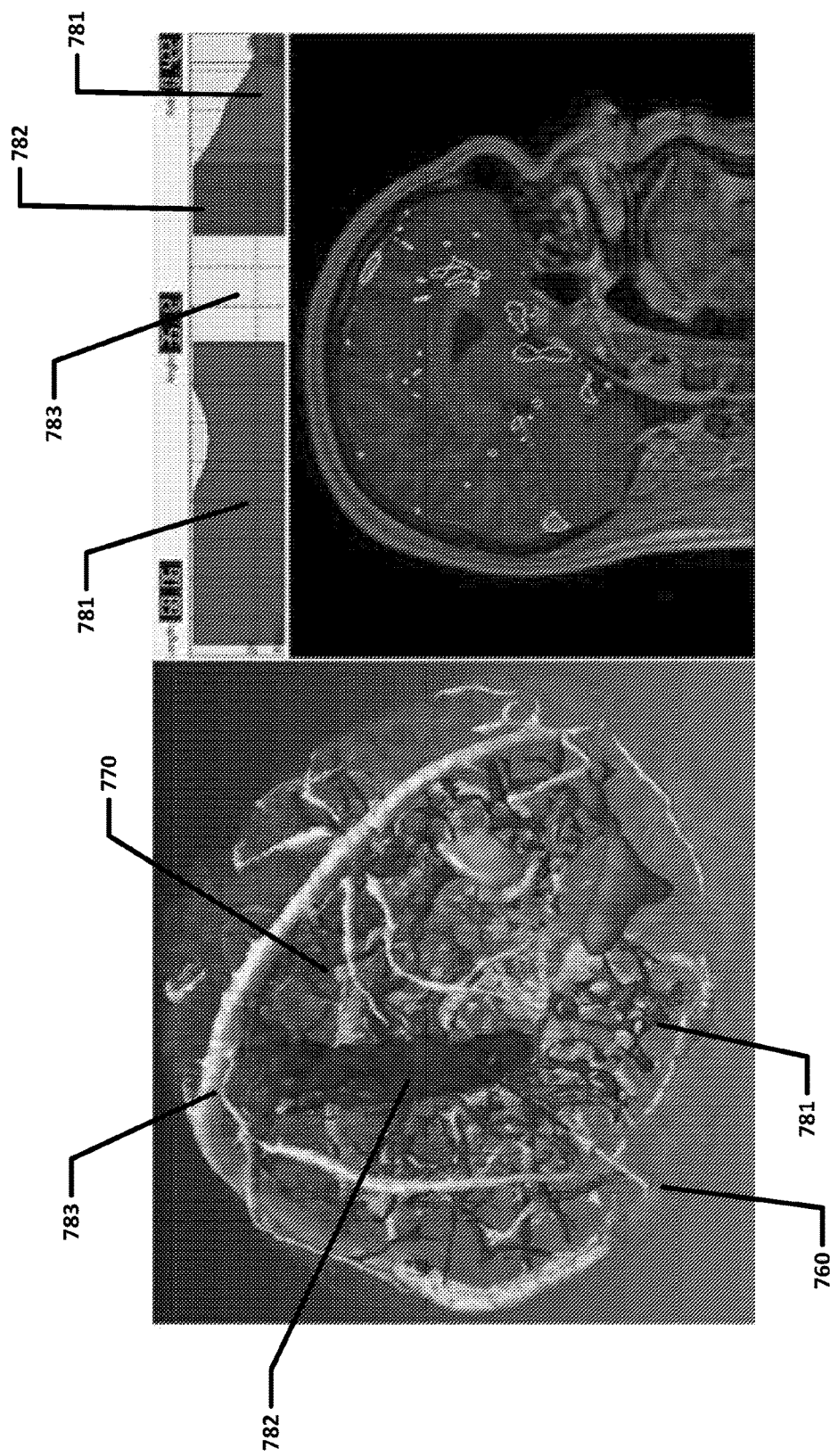
FIG. 7 is an example of a combination of linked visualisations provided by the tool of FIG. 1.

FIG. 7 is an example of the coordinated or linked visualisations. The left-hand diagram is a 3D representation, including a target point 770 and an entry point marker arrow 760. The top right portion is the distance graph (as per FIG. 5) between the entry point 760 and the target location 770. The lower right portion shows a corresponding 2-D (ortho) representation. Note that the distance graph has differently coloured regions to indicate the nature of the critical object that is closest to a given location along the trajectory—artery (red) 781, vein (cyan) 783 and cerebrospinal tract (blue) 610. (Corresponding regions of these three different types are also denoted using the same reference numerals in the left-hand 3-D representation, although the particular denoted regions are not intended to indicate the portions closest to the trajectory).

Post-Implantation 4D Seizure Analysis

Not only does the EpiNav system 100 provide support for pre-operative planning, but it also provides support for the analysis of the SEEG data which is subsequently acquired. Thus after the electrodes are implanted, the patient generally undergoes a CT scan. From this CT scan, the exact location of the electrodes and contacts can be determined. This information can be used as a gold standard for the validation of the plan. The electrodes can then be displayed by the EpiNav system 100 in these determined positions. The different electrodes are colour coded, thereby allowing ready discrimination of which electrode is which. In addition, the multiple contacts of each electrode are numbered (the deepest is number 1, as discussed above). The electrodes with their colour coding and contact numbers are displayed in both the 2D and 3D views; the electrodes themselves are displayed as surface objects, while the reference image and critical objects are volume rendered. This combination of the rendering methods allows the electrodes to be observed in context, without the other objects obstructing the view. This information can be used, inter alia, to determine how accurately the insertion followed the desired trajectory, which in turn can be used to help determine an appropriate safety margin for future insertions.

In addition, the intra-cranial EEG readings can be imported into the EpiNav system 100 and the signal amplitudes displayed as a time-sequence graph per electrode contact (timeline). The user is able to play back the sequences, scan forward/backward in time, and zoom in and out on a selected section of the time sequence graph. The 2D/3D visualization is synchronised to the EEG display. For example, the active contacts at a given time-point are highlighted, while the non-active electrodes are hidden to reflect the state when the signals were recorded. By using the playback option or scrolling through the time sequence, it is possible to follow the seizure onset. In particular, as the electric signal spreads and travels through different brain areas, different electrode contacts become active and highlighted in the 2D/3D displays.

To aid the selection of electrodes and contacts, and to ease the navigation within the 3D model, a grid display is utilised. Each column of the grid corresponds to an electrode, while each row of the grid corresponds to a contact. For example the $5^{th}$ contact of electrode 3 can be found in column 3, row 5. Clicking on any cell of the grid-display will re-align the visualization to focus on the selected contact. The grid display is also linked to the EEG timeline, so that when traversing through the time-points, the active trajectories are highlighted in the grid display, as well as in the 2D/3D windows.

The EpiNav system 100 also provides another form of visualization, in which all the electrode contacts are assigned a colour based on how frequently they are triggered. In this way, a 3D heat-map can be generated, which permits the easy identification of the most frequently triggered contacts, and also highlights the areas of the cortex that apparently played the most significant part in the development of the seizure.

Evaluation and Results

Computational Performance— the various methods described above have been tested several times using different input data, and the average execution time was recorded for each case. The dataset set used in the testing (evaluation) had 4 surface mesh representations (meshes): skull surface (185 k vertices); cerebrospinal tract (33 k vertices); veins (91 k vertices); and arteries (70 k vertices). The process times were recorded using OpenCL time events, including both the execution time of the OpenCL kernels, task execution scheduling and the time of data transfer between host workstation and device (GPU 125). The desktop (personal) computer 120 that was used in the tests has the following configuration: Intel XEON 16-core CPU, 16 GB of RAM and an NVidia Quadro K2000 2 GB GPU 125.

The first step of the risk analysis involves the entry point search, which aims to reduce the number of candidate trajectories. In particular, the first step filters out entry points that are more than a certain distance from the target entry point, have an unsuitable entry angle, or have a line of sight to the target point that passes through a critical structure. To test this first step, the skull surface model was loaded and 10 historical (i.e. previously utilised) electrode target points were selected. The average time to complete the analysis of the first step on the system described above was measured as 2.7 ms. This first step produced an average reduction factor of 97% in the number of candidate entry points. The number of candidate entry points remaining after this first step for the different target points typically fell in the range of 200-6000 entry point candidates.

The risk analysis then performs the construction of the BVH on the GPU. The processing time depends largely on the number of vertices used in the mesh representations of the critical structures. For the reference skull image (the largest surface mesh used in the test) the construction took 50 ms on average. As the BVH only needs to be constructed once, this calculation can be performed in advance if so desired, and hence does not affect the real-time performance.

The second step of the risk analysis, namely risk evaluation and aggregation, involves the evaluation of different trajectories based on the calculations specified in Equations 1 and 2. The computation time for performing this analysis was tested for various numbers of trajectories, which were generated by specifying a target point and assigning a number of random entry points from the software. The computation time was found to be an approximately linear function of the number of trajectory candidates, and even for the expected maximal number of entry points (~6000) the EpiNav system 100 is able to provide real-time interaction.

Table 1 presents the results of testing the first step of the analysis (entry point search) and also the second step of the analysis (risk evaluation and aggregation).

TABLE 1

Computation time for entry point search and risk evaluation for software-generated trajectories over the test dataset

| Total Number of Trajectories | Entry Point Search (ms) | Risk Evaluation and Aggregation (ms) |
|---|---|---|
| 1 | 2.4 | 1.3 |
| 5 | 2.3 | 7.1 |
| 50 | 2.1 | 13.4 |
| 500 | 2.7 | 96.7 |
| 5000 | 2.3 | 248.1 |

Neurosurgical Evaluations— in order to evaluate the benefits of employing the EpiNav system 100 for computer-assisted planning (based on the distance graph and risk estimation), the results of the computer-assisted planning have been compared with the results of a traditional (manual) planning approach for 6 electrode trajectories in six patients.

The analysis was performed using historical data, where the original trajectories were planned in a traditional way by expert neurosurgeons without using advanced computer-assisted planning. The average time to plan one electrode using such a non-assisted approach is estimated as 10-15 min based on our previous experience. The new trajectories were planned using the computer-assisted planning, keeping the same target points for the purpose of comparison. For each target point, the software analysed the topology of the critical structures to find potential entry points and computed the risks for them. Based on these risk values the system automatically offered an optimal entry point and resulting trajectory for each target point.

The new trajectories were inspected by a surgeon to validate the safety profile and feasibility. The trajectories were compared for length, angle of entry, risk value (as described above) and time taken to place. The entry point has changed in all cases, while the target point had to be adjusted in three cases (P2-T5, P3-T4, and P5-T4) when it had originally been placed too close to a critical structure so that the computer-assisted planning was not possible. Overall, the EpiNav system 100 provided a more feasible entry angle in all cases, while length of the trajectory was shorter in 57 of the 60 cases. The overall risk was smaller in 57 of the 60 cases using the EpiNav system, for the remaining 3 cases the risk was only marginally higher, and both angle and length values were better.

The general feedback from the surgeon was that the new system provides trajectories that are easier to implement in the theatre and have a lower risk profile. In addition, the required planning time was reduced to 2-3 min per electrode, which is approximately the time it takes for the surgeon to thoroughly inspect the full length of the planned trajectory.

Figure 8A:
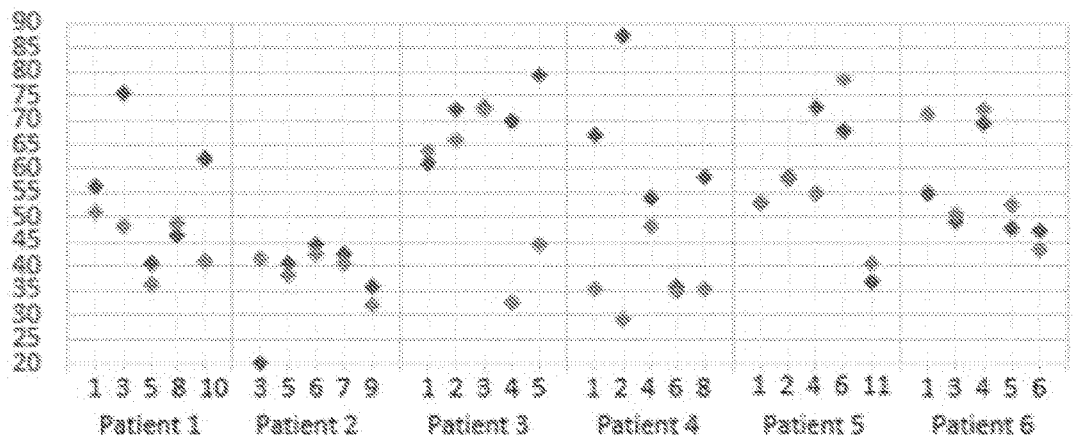
FIGS. 8A, 8B, and 8C are graphs showing the properties of the trajectories, in terms of length, entry angle, and risk respectively, for trajectories determined with and without computer-assisted planning (for a given target location).
Figure 8B:
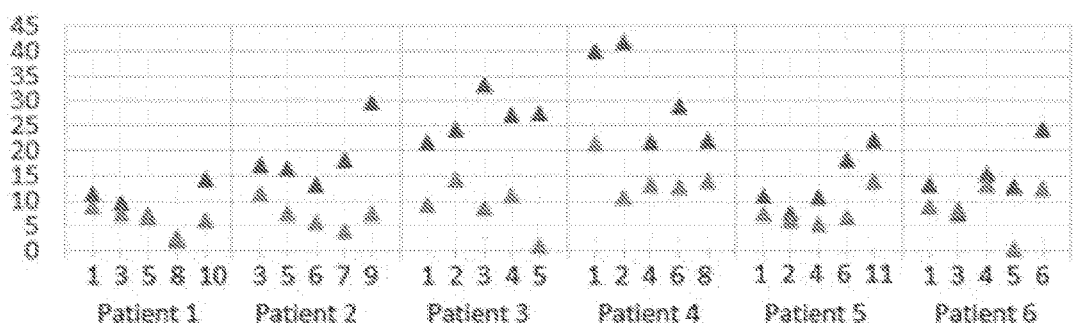
Figure 8C:
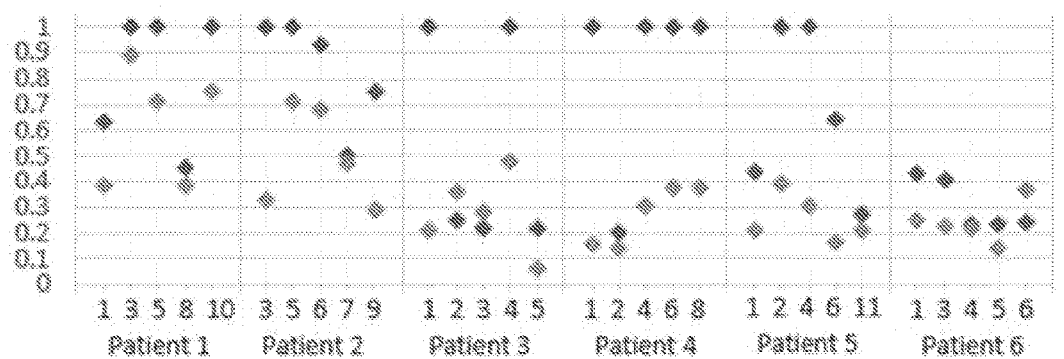

FIG. 8 compares the results for trajectories that were planned without AP (blue, generally higher symbols) against the results for trajectories that were planned using assisted planning as provided by the EpiNav system 100 (orange, generally lower symbols). In particular, FIG. 8A compares trajectory length, FIG. 8B compares entry angle offset (deviation from normal), while FIG. 8C compares calculated risk for the trajectory. It is readily apparent from these graphs that the trajectories that were planned using assisted planning as provided by the EpiNav system 100 are usually better than those that were planned without AP (for the same target location).

Figure 9:
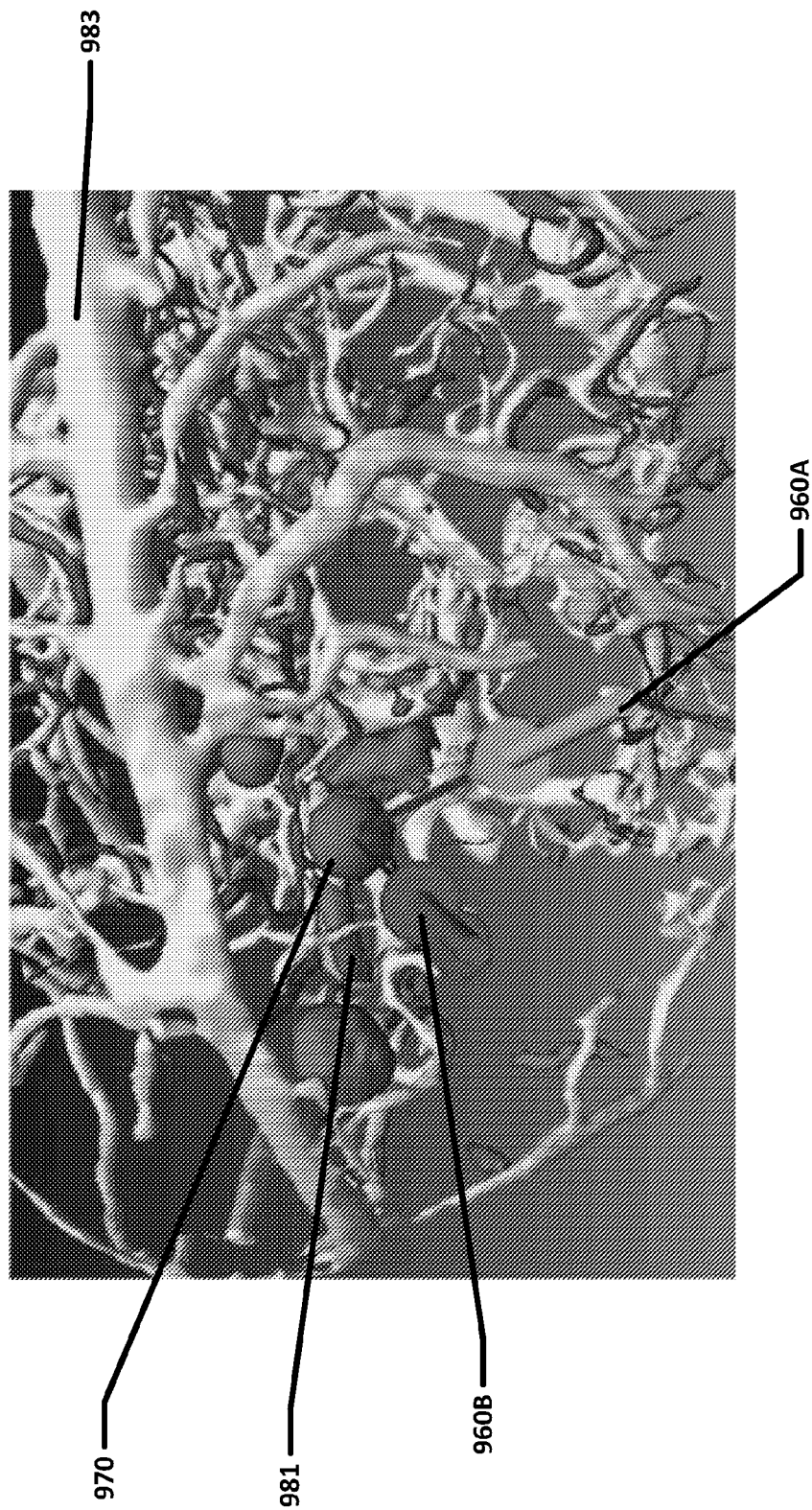
FIG. 9 is an illustration of the change in trajectory for a given target location resulting from the use of computer-assisted planning (compared with not using computer-assisted planning).

FIG. 9 shows the change in trajectory between a trajectory 960A (green) to a target location 970 that was planned without assistance to a trajectory 960B (purple) to the same target location that was planned using assisted planning as provided by the EpiNav system 100. The new (computer-assisted) trajectory 960B has been found to provide better separation from the blood vessels, namely arteries 981 (red) and veins 983 (cyan), thereby reducing the risk of the surgical incision to this target location 970.

CONCLUSION

In conclusion, the computer-assisted SEEG planning system (EpiNav) described herein helps to find safer trajectories which are easier to implement and which provide a surgeon with greater confidence in the trajectory of each individual electrode. The GPU-based implementation enables real-time interaction and risk evaluation that reduces planning time and allows a more efficient clinical workflow. The quality of output from the computer-assisted planning is dependent on the quality of input, in particular regarding the segmented surfaces that are used to represent the skull and critical surface. As new imaging and segmentation tools become available, the quality of this input to the computer-assisted planning will become increasingly higher, thereby further improving the reliability of the computer-assisted planning results.

Various embodiments of the invention have been described above. The skilled person will appreciated that the features of these embodiments may be combined with one another as appropriate, or modified according to the particular circumstances of any given application. The scope of the invention is defined by the appended claims and their equivalents.

ACKNOWLEDGMENTS

This work represents independent research supported by the Health Innovation Challenge Fund (HICF-T4-275), a parallel funding partnership between the Department of Health and Wellcome Trust. The views expressed herein are those of the inventor(s) and not necessarily those of the Department of Health or Wellcome Trust.

REFERENCES

1. Sirven J I, et al. (2011) Evaluation and management of drug-resistant epilepsy. Available at: http://www.uptodate.com/contents/evaluation-and-management-of-drugresistant-epilepsy. Accessed Nov. 22, 2013
2. Devinsky, Orrin. "Patients with refractory seizures." New England Journal of Medicine 340.20 (1999): 1565-1570.
3. David, Olivier, et al. "Imaging the seizure onset zone with stereo-electroencephalography." Brain 134.10 (2011): 2898-2911.
4. Rosenow, Felix, et al. "Presurgical evaluation of epilepsy." Brain 124.9 (2001): 1683-1700.

5. Olivier, André, et al. Techniques in epilepsy surgery: the MNI approach. Cambridge University Press, 2012.
6. S. B'eriault, et al. "Automatic trajectory planning of DBS neurosurgery from multimodal MRI datasets," in Proc. of Medical Image Computing and Computer-Assisted Intervention—MICCAI 2011. Springer, 2011, pp. 259-266.
7. C. Essert, et al., "Automatic computation of electrodes trajectory for deep brain stimulation," in Proc. Of Medical Imaging and Augmented Reality—5th International Workshop, MIAR 2010. Springer, 2010, pp. 149-158.
8. C. Essert, et al. "Automatic computation of electrode trajectories for deep brain stimulation: a hybrid symbolic and numerical approach," Int'l J. of Comp. Assist. Rad. and Surg., vol. 7, no. 4, pp. 517-532, 2011.
9. N. V. Navkar, et al. "Visualization and planning of neurosurgical interventions with straight access," in Proc. of International Conference on Information Processing in Computer-Assisted Interventions—IPCAI'10. Berlin, Heidelberg: Springer-Verlag, 2010, pp. 1-11.
10. R. R. Shamir, et al. "A method for planning safe trajectories in image-guided keyhole neurosurgery," in Proc. of Medical Image Computing and Computer-Assisted Intervention—MICCAI 2010. Springer, 2010, pp. 457-464
11. Bériault, Silvain, et al. "A multi-modal approach to computer-assisted deep brain stimulation trajectory planning." International journal of computer assisted radiology and surgery 7.5 (2012): 687-704.
12. Herghelegiu, Paul-Corneliu, et al. "Biopsy Planner-Visual Analysis for Needle Pathway Planning in Deep Seated Brain Tumor Biopsy." Computer Graphics Forum. Vol. 31. No. 3 pt 2. Blackwell Publishing Ltd, 2012.
13. Rincon, Mario, et al. "GPU-Accelerated Interactive Visualization and Planning of Neurosurgical Interventions." (2013): 1-1.
14. Wolf, Ivo, et al. "The medical imaging interaction toolkit." Medical image analysis 9, no. 6 (2005): 594-604.
15. Rodionov, Roman et al. "Feasibility of multimodal 3D neuroimaging to guide implantation of intracranial EEG electrodes." *Epilepsy research* (2013).
16. Burgos, Ninon, et al. "Attenuation Correction Synthesis for Hybrid PET-MR Scanners." *Medical Image Computing and Computer-Assisted Intervention—MICCAI 2013*. Springer Berlin Heidelberg, 2013. 147-154.
17. Lauterbach, C., et al. (2009, April). Fast BVH construction on GPUs. In *Computer Graphics Forum* (Vol. 28, No. 2, pp. 375-384). Blackwell Publishing Ltd.
18. Karras, Tero. "Maximizing parallelism in the construction of BVHs, octrees, and k-d trees." *Proceedings of the Fourth ACM SIGGRAPH/Eurographics conference on High-Performance Graphics*. Eurographics Association, 2012.

What is claimed is:

1. A method of using a computer system to assist in planning a trajectory for a surgical insertion into a skull, the method comprising:
providing the computer system with a three-dimensional representation of the skull and of critical objects located within the skull, wherein said critical objects comprise anatomical features to be avoided during the surgical insertion;
providing the computer system with a target location for the insertion within the skull;
selecting an entry point representing a surface location on the skull;
determining by the computer system for the entry point an associated trajectory from the entry point to the target location;
calculating by the computer system a risk factor for said entry point by integrating f(x) along the trajectory associated with the entry point, where x represents distance along the trajectory to a sample point, and f(x) is a function based on distance from the sample point at distance x to a critical object which is nearest to said sample point;
wherein selecting an entry point comprises generating by the computer system a plurality of entry points, each entry point representing a surface location on the skull, each entry point being associated with a trajectory from the entry point to the target location, and wherein said step of assessing is performed for each of said plurality of entry points; and
wherein the step of generating produces a first set of entry points, and the step of assessing is performed with respect to a second, reduced set of entry points, and the method further comprises discarding by the computer system entry points from the first set to form the second set, wherein an entry point is discarded from the first set of entry points if the entry point has an entry angle which fails a condition for being substantially perpendicular to the skull surface.

2. The method of claim 1, further comprising assessing by the computer system the entry point against a set of one or more risk criteria, wherein the set of one or more criteria includes the risk factor calculated by integrating f(x) along the trajectory associated with the entry point.

3. The method of claim 2, further comprising providing a plurality of target locations, and wherein said one or more criteria for assessing a trajectory include ensuring that the trajectories to respective target locations do not conflict with one another.

4. The method of claim 3, wherein said ensuring comprises, for a set of N target locations, having an arbitrary ordering:
1) start with n=1;
2) select an nth target point;
3) add the lowest risk trajectory for the nth target point;
4) evaluate to see if there is a conflict between the n selected trajectories;
5) if so, find the combination of trajectories having the next lowest risk and return to (4);
6) else increment n by 1;
7) if n>N, exit; and
8) else return to (2).

5. The method of any of claim 3, wherein there is a conflict between two trajectories if they pass within a predetermined distance of one another.

6. The method of claim 1, wherein the function f(x) denotes a cost function that has a value of zero (minimum cost) when the distance from the sample point to the nearest critical object is greater a first predetermined threshold distance which defines a risk zone.

7. The method of claim 6, wherein the function f(x) denotes a cost function that has a value of one (maximum cost) when the distance from the sample point to the nearest critical object is less than a second predetermined threshold distance which defines a safety margin.

8. The method of claim 7, wherein the function f(x) rises in linearly with distance from the sample point to the nearest critical object between the first predetermined threshold distance and the second predetermined threshold distance.

9. The method of claim 1, further comprising defining a plurality of sample points along the trajectory associated with an entry point, and integrating f(x) along the trajectory comprises summing the value of f(x) at each of said plurality of sample points.

10. The method of claim 1, further comprising the computer system providing a graphical visualization of a trajectory, said visualization illustrating how the distance from a sample point at distance x along the trajectory to the critical object which is nearest to the sample point varies with x along the trajectory.

11. The method of claim 10, wherein said graphical visualization includes an indication of a first predetermined threshold distance which defines a risk zone for a critical object and a second predetermined threshold distance which defines a safety margin.

12. The method of claim 10, wherein said graphical visualization of a trajectory is linked to at least one two-dimensional or three-dimensional view derived by the computer system from the three-dimensional representation of the skull and of critical objects located within the skull, such that selecting a location along the trajectory causes the computer system to generate said at least one two-dimensional or three-dimensional view so as to include or be taken from said location.

13. The method of claim 1, wherein providing a target location comprises identifying by the user an anatomical region, structure or feature within the skull, and the computer system selecting a target location within said anatomical region, structure or feature within the skull.

14. A method of using a computer system to assist in planning a trajectory for a surgical insertion into a skull, the method comprising:
providing the computer system with a three-dimensional representation of the skull and of critical objects located within the skull, wherein said critical objects comprise anatomical features to be avoided during the surgical insertion;
providing the computer system with a target location for the insertion within the skull;
generating by the computer system a first set comprising a plurality of entry points, each entry point representing a surface location on the skull, and each entry point being associated with a trajectory from the entry point to the target location;
discarding by the computer system entry points from the first set to form a second, reduced set comprising a plurality of entry points, wherein an entry point is discarded from the first set of entry points if the entry point has an entry angle which fails a condition for being substantially perpendicular to the skull surface; and
for each entry point in the second set, assessing by the computer system said entry point against a set of one or more criteria, wherein the set of one or more criteria includes a risk factor based on the separation between the critical objects and the trajectory which is associated with said entry point;
providing a graphical visualization of a trajectory, said visualization illustrating how the distance from a sample point at distance x along the trajectory to the critical object which is nearest to the sample point varies with x along the trajectory; and
providing a plurality of target locations, and wherein the set of one or more criteria for assessing a trajectory to a given target location include determining that the trajectory does not conflict with a trajectory to any other target location.

15. The method of claim 14, wherein assessing by the computer system said entry point against a set of one or more criteria comprises calculating by the computer system a risk factor for said entry point by integrating f(x) along the trajectory associated with the entry point, where x represents distance along the trajectory to a sample point, and f(x) is a function based on distance from the sample point at distance x to a critical object which is nearest to said sample point.

16. The method of claim 14, wherein said condition for being substantially perpendicular to the skull surface requires the entry angle to be within a predetermined angular distance of the normal to the skull surface at the entry point.

17. The method of claim 14, wherein said discarding further comprises discarding an entry point from the first set if the trajectory associated with the entry point exceeds a predetermined length.

18. The method of claim 14, wherein said discarding further comprises discarding an entry point from the first set if the trajectory associated with the entry point passes through a critical object.

19. The method of claim 14, wherein said one or more criteria include a risk factor based on entry angle for an entry point and a risk factor based on the length of the trajectory associated with an entry point.

20. The method of claim 14, wherein said one or more criteria include a cost function based on the proportion of the trajectory associated with an entry point which passes through grey matter compared with the proportion of said trajectory which passes through white matter.

21. The method of claim 14, further comprising, based on said assessment, selecting by the computer system an entry point and associated trajectory for use in the surgical incision, and providing a graphical representation of the selected trajectory in at least one two-dimensional or three-dimensional view derived by the computer system from the three-dimensional representation of the skull.

22. The method of claim 14, further comprising imaging the incision when performed and the critical objects to compare the path of the incision with the planned trajectory.

23. The method of claim 14, wherein the surgical incision is to implant an electrode for performing stereo-electroencephalography, or wherein the surgical incision is to insert a stent, or wherein the surgical incision is to perform deep brain stimulation or a tumor biopsy.

24. Apparatus comprising a computer system configured to assist in planning a trajectory for a surgical insertion into a skull, the computer system being configured to:
provide the computer system with a three-dimensional representation of the skull and of critical objects located within the skull, wherein said critical objects comprise anatomical features to be avoided during the surgical insertion;
provide the computer system with a target location for the insertion within the skull;
select an entry point representing a surface location on the skull;
determine by the computer system for the entry point an associated trajectory from the entry point to the target location;
calculate by the computer system a risk factor for said entry point by integrating f(x) along the trajectory associated with the entry point, where x represents distance along the trajectory to a sample point, and f(x)

is a function based on distance from the sample point at distance x to a critical object which is nearest to said sample point;

wherein the step of generating produces a first set of entry points, and the step of assessing is performed with respect to a second, reduced set of entry points, and the method further comprises discarding by the computer system entry points from the first set to form the second set, wherein an entry point is discarded from the first set of entry points if the entry point has an entry angle which fails a condition for being substantially perpendicular to the skull surface; and provide a graphical visualization of a trajectory, said visualization illustrating how the distance from a sample point at distance x along the trajectory to the critical object which is nearest to the sample point varies with x along the trajectory.

* * * * *